(12) United States Patent  
Burnes et al.

(10) Patent No.: US 7,010,344 B2
(45) Date of Patent: Mar. 7, 2006

(54) METHOD AND APPARATUS FOR DELAYING A VENTRICULAR TACHYCARDIA THERAPY

(75) Inventors: John E. Burnes, Andover, MN (US); Paul J. DeGroot, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 545 days.

(21) Appl. No.: 10/134,352

(22) Filed: Apr. 26, 2002

(65) Prior Publication Data

US 2003/0204209 A1    Oct. 30, 2003

(51) Int. Cl.
    *A61N 1/39*    (2006.01)
(52) U.S. Cl. ............................... 607/4; 607/5
(58) Field of Classification Search ............... 607/4–5, 607/18–19, 23, 25
    See application file for complete search history.

(56) References Cited

U.S. PATENT DOCUMENTS

| | | | | |
|---|---|---|---|---|
| 4,559,947 A | * | 12/1985 | Renger et al. ................ | 607/9 |
| 4,830,006 A | | 5/1989 | Haluska et al. ............... | 607/4 |
| 5,117,824 A | | 6/1992 | Keimel et al. ................ | 607/4 |
| 5,163,429 A | * | 11/1992 | Cohen ........................... | 607/4 |
| 5,191,884 A | | 3/1993 | Gilli et al. ...................... | 607/5 |
| 5,205,283 A | | 4/1993 | Olson ............................. | 607/4 |
| 5,233,984 A | | 8/1993 | Thompson ................... | 607/18 |
| 5,545,186 A | | 8/1996 | Olson et al. ................. | 607/14 |
| 5,593,431 A | | 1/1997 | Sheldon ........................ | 607/19 |
| 5,630,834 A | | 5/1997 | Bardy ............................ | 607/5 |
| 5,987,356 A | | 11/1999 | DeGroot ........................ | 607/5 |
| 6,044,297 A | | 3/2000 | Sheldon et al. ............... | 607/17 |
| 6,067,473 A | | 5/2000 | Greeninger et al. .......... | 607/32 |
| 6,128,526 A | | 10/2000 | Stadler et al. .............. | 600/517 |
| 6,171,252 B1 | | 1/2001 | Roberts ...................... | 600/485 |
| 6,221,024 B1 | | 4/2001 | Miesel ........................ | 600/486 |
| 6,711,442 B1 | * | 3/2004 | Swerdlow et al. ............ | 607/63 |

FOREIGN PATENT DOCUMENTS

EP    0 815 900    1/1998

* cited by examiner

*Primary Examiner*—Carl Layno
(74) *Attorney, Agent, or Firm*—Girma Wolde-Michael; Michael C. Soldner

(57) ABSTRACT

A device and method to detect slow ventricular tachycardia, deliver anti-tachycardia pacing therapies, and delay a scheduled shock therapy if the ventricular tachycardia is not terminated or accelerated. Preferably, a shock therapy is delayed after verifying hemodynamic stability based on a hemodynamic sensor. After a shock is delayed, the device operates in a high alert mode for redetecting an accelerated tachycardia. Anti-tachycardia pacing therapies are repeated during the shock delay. A number of conditions can trigger delivery of the delayed shock therapy including a specified period of elapsed time; determination that the patient is likely to be asleep; detection of myocardial ischemia; detection of compromised hemodynamics, or detection of a substantially prone position or sudden change in position. A delayed shock therapy may be triggered by the patient and repeated delivery of painful shock therapies in patients that are not seriously compromised by a recurring, slow ventricular tachycardia is avoided.

15 Claims, 7 Drawing Sheets

METHOD AND APPARATUS FOR DELAYING A VENTRICULAR TACHYCARDIA THERAPY

FIELD OF THE INVENTION

The present invention relates to an implantable cardiac stimulation device capable of delivering anti-tachycardia therapy and more specifically a device and method for delaying shock therapies when a detected slow ventricular tachycardia is determined to be stable.

BACKGROUND

Implantable medical devices are available for treating cardiac arrhythmias by delivering electrical shock therapy for cardioverting or defibrillating the heart in addition to cardiac pacing. Such a device, commonly known as an implantable cardioverter defibrillator or "ICD", senses a patient's heart rhythm and classifies the rhythm according to a number of rate zones in order to detect episodes of tachycardia or fibrillation. Single chamber devices are available for treating either atrial arrhythmias or ventricular arrhythmias, and dual chamber devices are available for treating both atrial and ventricular arrhythmias. Rate zone classifications typically include normal sinus rhythm, tachycardia, and fibrillation.

Upon detecting an abnormal rhythm, the ICD delivers an appropriate therapy. Cardiac pacing is delivered in response to the absence of sensed intrinsic depolarizations, referred to as P-waves in the atrium and R-waves in the ventricle. Ventricular fibrillation (VF) is a serious life-threatening condition and is normally treated by immediately delivering high-energy shock therapy. Termination of VF is normally referred to as "defibrillation."

In response to tachycardia detection, a number of tiered therapies may be delivered beginning with anti-tachycardia pacing therapies and escalating to more aggressive shock therapies until the tachycardia is terminated. Termination of a tachycardia is commonly referred to as "cardioversion." In modern implantable cardioverter defibrillators, the physician programs the particular therapies into the device ahead of time, and a menu of therapies is typically provided. For example, on initial detection of an atrial or ventricular tachycardia, an anti-tachycardia pacing therapy may be selected and delivered to the chamber, in which the tachycardia is diagnosed or to both chambers. On redetection of tachycardia, a more aggressive anti-tachycardia pacing therapy may be scheduled. If repeated attempts at anti-tachycardia pacing therapies fail, a higher energy cardioversion pulse may be selected. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. For an overview of tachycardia detection and treatment therapies reference is made to U.S. Pat. No. 5,545,186 issued to Olson et al.

Ventricular tachycardia (VT) may be debilitating, but is not necessarily an immediately life-threatening situation. Cardiac output tends to be compromised due to the disorganized contraction of the myocardial tissue resulting in a patient feeling weak, dizzy or even fainting. Ventricular tachycardia may, however, degenerate into a more unstable heart rhythm, leading to ventricular fibrillation. Therefore in most cases, it is desirable to immediately treat a detected VT, either with anti-tachycardia pacing therapies or cardioversion shocks. Because VT can often be terminated by known anti-tachycardia pacing therapies, these therapies are generally delivered first, because they are less painful to the patient, then followed by high-energy shock therapy if necessary.

However, in some cases, a patient may be diagnosed with a recurrent slow-rate ventricular tachycardia that is not associated with symptoms of hemodynamic compromise. When a recurrent VT is repeatedly detected by an ICD device, the patient will normally undergo a preset menu of tiered therapies, which may conclude with shock delivery in order to terminate the VT. Therefore, a patient having a recurrent VT may be repeatedly subjected to painful shock therapies. In a patient having recurrent, but hemodynamically stable, slow VT, such repeated shock therapy may be undesirable since the condition is not immediately life-threatening and not expected to deteriorate into a more serious tachycardia. An implantable cardioverter defibrillator device capable of delaying or suspending a high-energy shock therapy in response to detecting a stable, low-rate ventricular tachycardia is therefore needed.

SUMMARY

The present invention addresses, inter alia, this problem of repeated shock delivery in patients having stable, low rate ventricular tachycardia. Aspects of the present invention include delaying the delivery of painful shock therapy in patients having recurrent slow VT, particularly when the patient is determined not to be hemodynamically compromised. Further aspects of the present invention include controlling the time of shock therapy delivery, so that non-critical shocking therapies are delivered at a time that the patient is not at further risk of injury or pain, and potentially averting the need for shock therapy by allowing continued attempts of anti-tachycardia pacing therapies to terminate the abnormal rhythm prior to delivering a delayed shock therapy.

These aspects are realized by providing an implantable medical device for delivering anti-tachyarrhythmia and defibrillation therapies to the heart, and specifically to the ventricles, in the form of pacing or shocking pulses and an associated method for discriminating between a low-rate or stable form of ventricular tachycardia and other, higher rate or unstable forms of ventricular tachycardia. An associated method includes first delivering anti-tachycardia pacing therapies when a slow, stable ventricular tachycardia is detected and delaying a programmed shock therapy.

The present invention includes a "high alert" mode executed during the period of delayed shock therapy to allow prompt therapy delivery should the heart rhythm accelerate or should other conditions arise indicating a need for shock therapy. During the high alert mode, less stringent redetection criteria is used than during normal device operation for arrhythmia detection. For example, the high alert redetection criteria may require fewer intervals within a VT or VF zone to allow for more rapid detection and therapy response.

The methods included in the present invention are enhanced by implementing a sensor of hemodynamic function. Detection of a VT with confirmation of stable hemodynamic function justifies delaying a shock therapy to a later time. Detection of a VT with decreased hemodynamic function, however, indicates a need for more immediate therapy. A delayed shock therapy is immediately delivered if compromised hemodynamic function is detected. During the delay period, anti-tachycardia pacing therapies are repeated in an attempt to restore the heart to normal sinus rhythm and avert the need for any shocking therapy.

Another feature of the present invention includes the programmable selection of conditions under which a delayed shock therapy is delivered in order to regain hemodynamic support or avoid the development of myocardial ischemia. For example, a delayed shock may be delivered after a specified period of elapsed time or after determining that the patient is likely to be resting or asleep. A delayed shock may be delivered upon detection of myocardial ischemia or detection of a substantially prone position or sudden change in position indicating that the patient may have fallen due to compromised hemodynamic output. A patient or physician issued command may also trigger a delayed shock therapy.

One aspect of the present invention is the ability to choose between conventional treatment modalities of escalating therapies or delaying more aggressive shock therapies in patients who are diagnosed with hemodynamically stable ventricular tachycardia. Repeated delivery of painful shock therapies in patients that are not seriously compromised by a recurring, stable, low-rate tachyarrhythmia is avoided. By avoiding frequently repeated shock therapies, the life-expectancy of the battery-powered implantable device is extended, and battery charge is reserved for more serious, life-threatening occurrences of tachycardia or fibrillation. Furthermore, the present invention allows the shock therapy to be delivered at a controlled time, for example, after the patient has had time to seek medical attention or at a time when the patient is not at risk of further injury, such as while driving a car.

DETAILED DESCRIPTION OF THE PREFERRED EMBODIMENTS

The present invention relates to a system and method for delaying shock therapies upon detection of a slow, stable ventricular tachycardia. The methods included in the present invention are preferably incorporated in an implantable cardiac stimulation device capable of delivering anti-arrhythmia therapies, such as the implantable cardioverter defibrillator, or "ICD," shown in FIG. 1.

Figure 1:
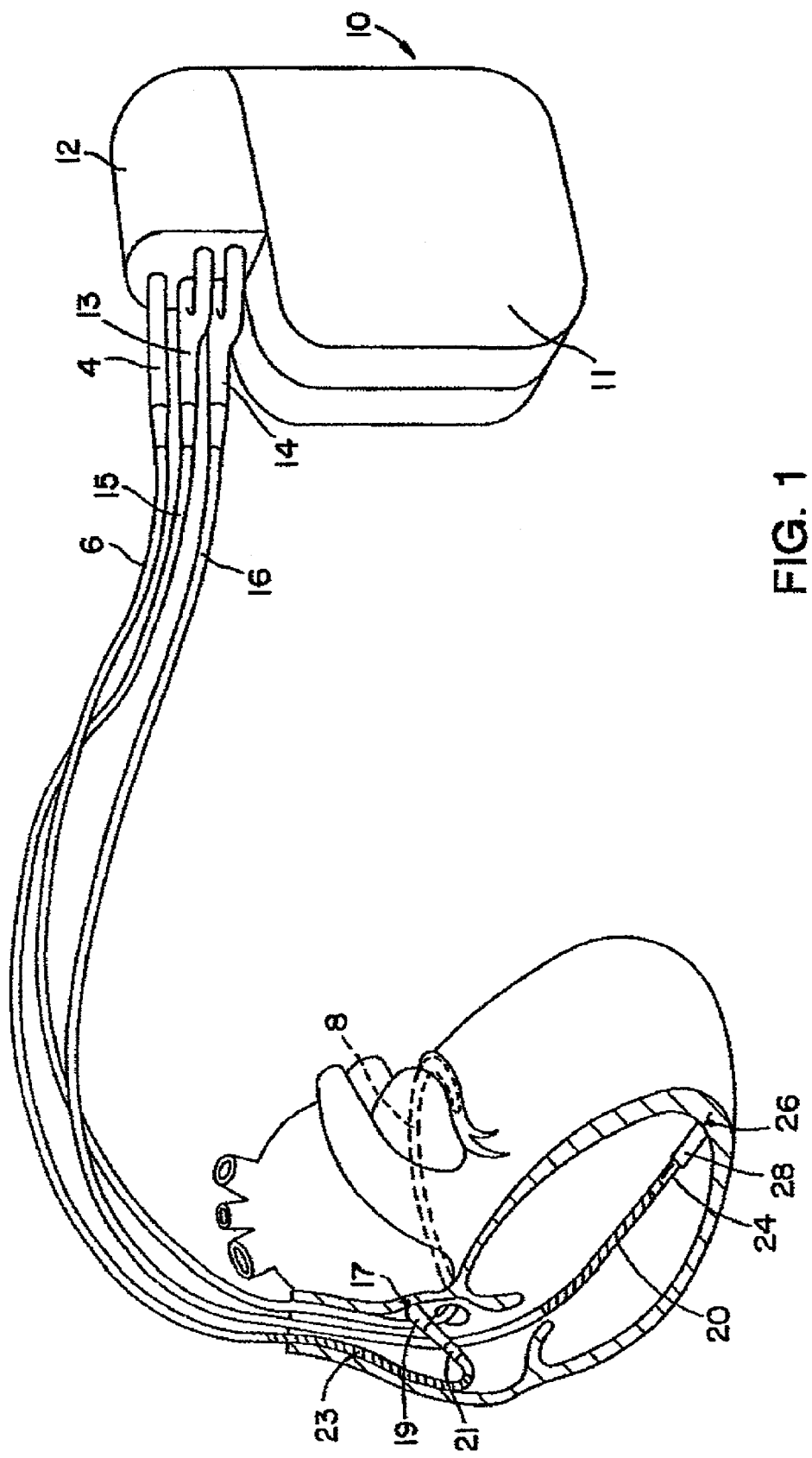
FIG. 1 is an illustration of an implantable cardiac stimulation device capable of pacemaking, cardioversion, and defibrillation and in communication with a patient's heart via three stimulation and sensing leads.

The ICD 10 is shown coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the vicinity of the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor within the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ing" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the coil electrodes 8, 20 or 23 for defibrillation of the atria or ventricles. It is recognized that alternate lead systems may be substituted for the three lead system illustrated in FIG. 1.

Although three or four-chamber pacing, cardioversion and defibrillation capacity is not necessary for practicing the invention, and indeed detection of slow ventricular tachycardia can be determined by sensing only signals derived from the right ventricle, a multi-chamber system is illustrated so as to indicate the scope of the invention. It is understood that the invention may normally be practiced with a multi-chamber, dual chamber, or single chamber device.

Figure 2:
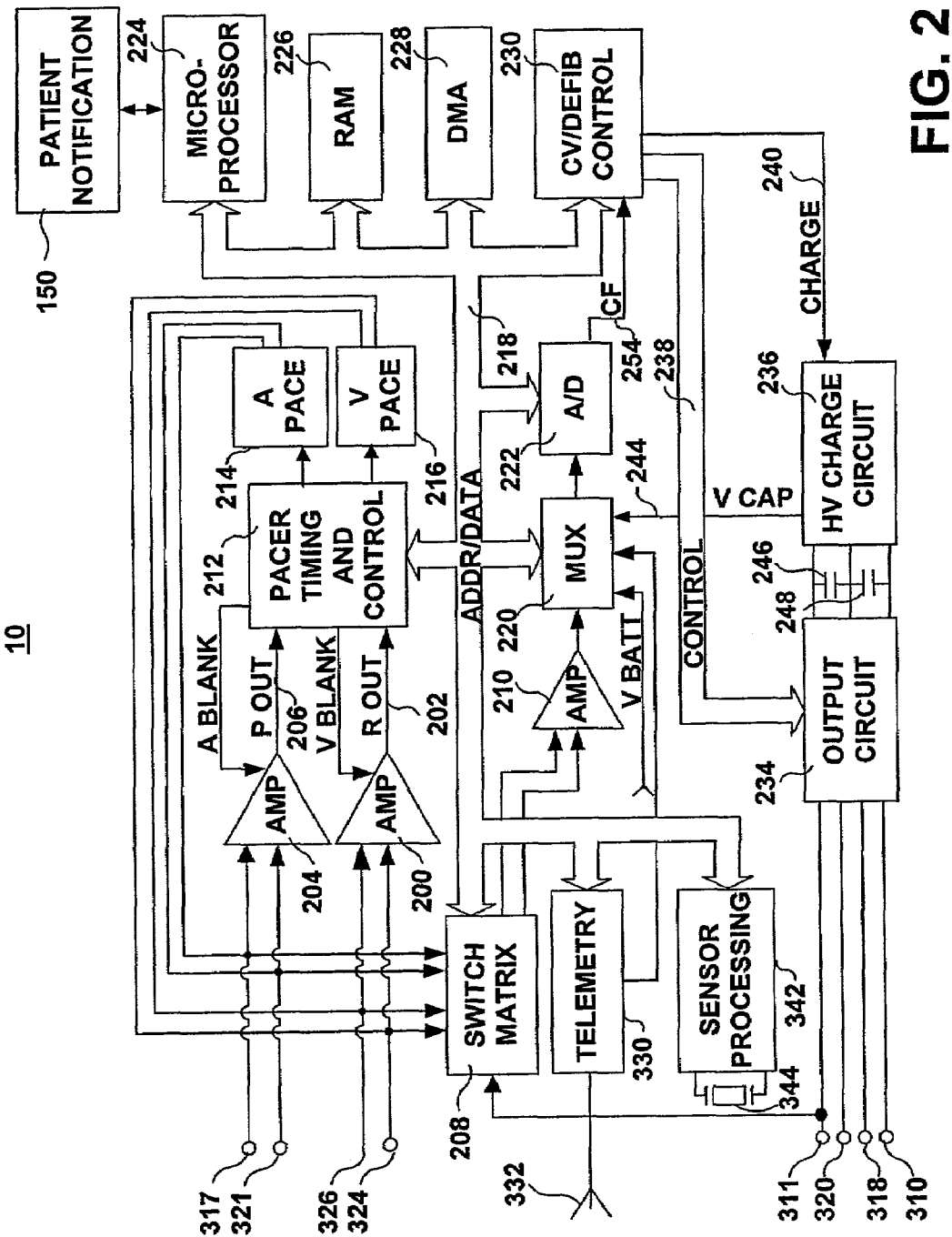
FIG. 2 is a high-level, functional, block diagram of the implantable pacemaker cardioverter defibrillator shown in FIG. 1.

A functional schematic diagram of the ICD 10 is shown in FIG. 2. This diagram should be taken as exemplary of the type of device in which the invention may be embodied and not as limiting. The disclosed embodiment shown in FIG. 2 is a microprocessor-controlled device, but the methods of the present invention may also be practiced in other types of devices such as those employing dedicated digital circuitry.

With regard to the electrode system illustrated in FIG. 1, the ICD 10 is provided with a number of connection terminals for achieving electrical connection to the leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206.

Whenever a signal received by the ventricular sense amplifier 200 exceeds a ventricular sensing threshold, a signal is generated on the R-out signal line 202. Switch matrix 208 is used to select which of the available electrodes are coupled to a wide band amplifier 210 for use in digital signal analysis.

Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art. A tachyarrhythmia recognition mechanism is described in U.S. Pat. No. 5,987,356, issued to DeGroot and in the previously referenced U.S. Pat. No. 5,545,186 issued to Olson et al, both of which patents are incorporated herein by reference in their entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known for use in implantable devices may be used. The telemetry circuit 330 is also used for communication with a patient activator in one embodiment of the present invention.

In a preferred embodiment, the device 10 is equipped with a sensor 344 and sensor processing circuitry 342. Depending on the type of sensor used, the sensor 344 may be located within the device housing 11 or external to the device housing 11 but implanted within the body of the patient. In one embodiment, the sensor 344 is used for determining the hemodynamic status of the patient. The sensor 344 may therefore be a pressure sensor for sensing a patient's blood pressure within the heart chambers or vasculature, an impedance sensor for sensing thoracic impedance, a blood oxygen sensor, a blood pH sensor, or any known sensor, or combination of sensors, capable of providing a signal that can be correlated to a patient's hemodynamic status. Pressure sensors that may be implemented with the ICD 10 for monitoring hemodynamic status are generally described in U.S. Pat. No. 6,171,252 to Roberts, and U.S. Pat. No. 6,221,024 to Miesel, both patents incorporated herein by reference in their entirety. In accordance with one embodiment of the present invention, signals received by the sensor processing circuit 342 from the sensor 344 can be analyzed for detecting a change in a patient's hemodynamic status particularly during a detected slow VT, as will be described in greater detail below.

In an alternative embodiment, the sensor 344 takes the form of a positional sensor for determining the posture of the patient. A method and apparatus for determining the physical posture of a patient's body is disclosed in U.S. Pat. No. 6,044,297 to Sheldon et al., incorporated herein by reference in its entirety. In one embodiment of the present invention, detection of a substantially prone position, or preferably a sudden change in position occurring after a VT detection, is used to determine that a patient may have fallen as a result of compromised hemodynamic status. In another embodiment of the present invention, a posture sensor may be used in combination with the time of day or an activity sensor for determining when the patient is asleep. Reference is made to U.S. Pat. No. 5,233,984 issued to Thompson, U.S. Pat. No. 5,593,431 issued to Sheldon, and U.S. Pat. No. 5,630,834 issued to Bardy, all of which are incorporated herein by reference in their entirety. Therefore, in certain embodiments, sensor 344 may represent a combination of sensors such as a pressure sensor, an activity sensor, and a posture sensor such that a change in hemodynamic status and/or sleep and/or posture may be detected by microprocessor 224

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated ROM in which stored programs controlling the operation of the microprocessor 224 reside. A portion of the memory 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microcontroller 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150 used to notify the patient that shock therapy is being withheld. Any patient notification method known in the art may be used, such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
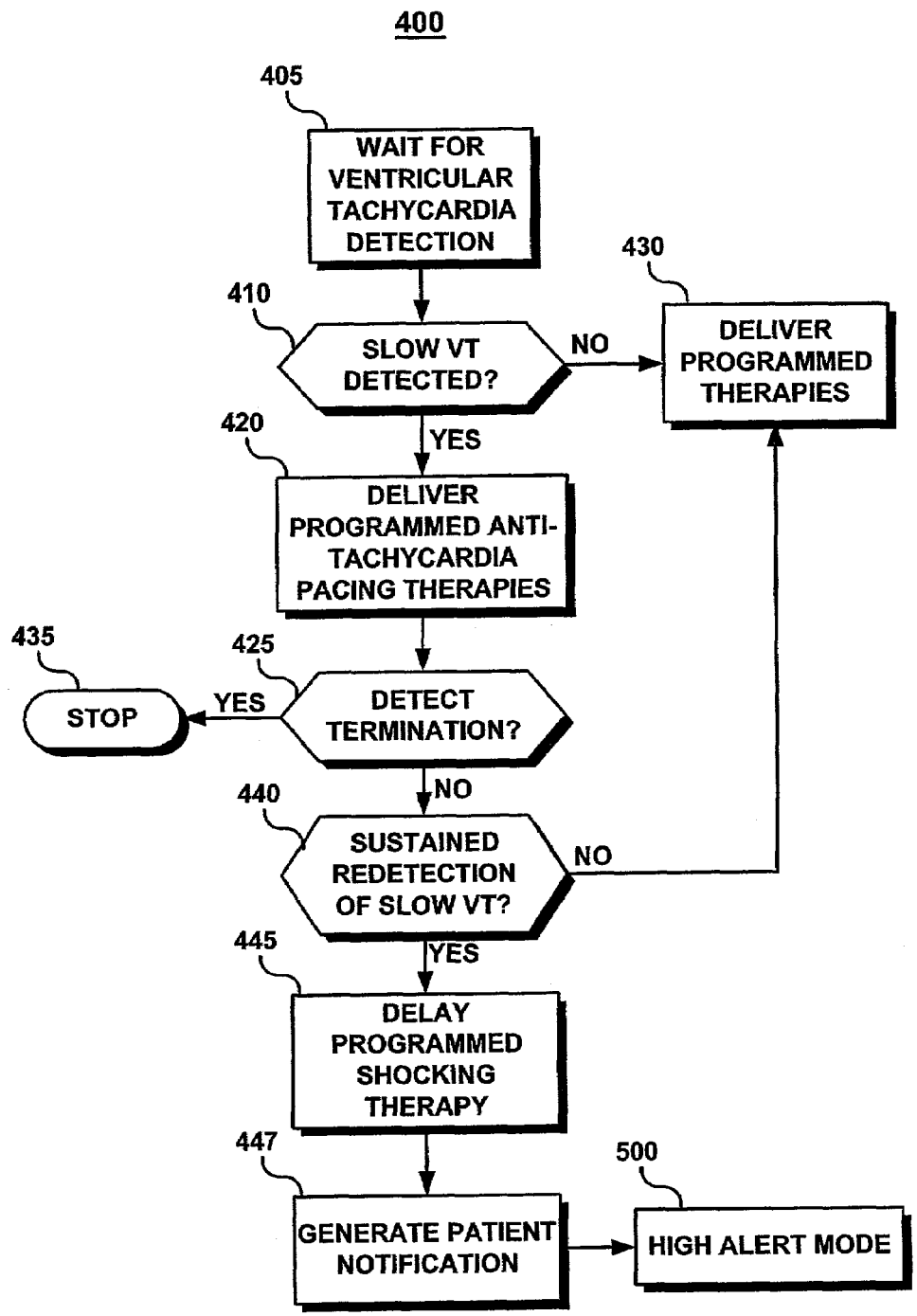
FIG. 3 is a flow chart illustrating a method performed by the device shown in FIG. 2 for delaying a ventricular tachycardia therapy according to one embodiment of the present invention.

In FIG. 3 a flow diagram is shown illustrating operations included in one embodiment of the present invention for delaying a programmed shock therapy in response to detecting a slow ventricular tachycardia. The steps illustrated in FIG. 3 are preferably carried out under the control of microprocessor 224. The method 400 is preferably enabled or disabled by a telemetered command delivered by a physician using an external programmer in communication with telemetry circuit 330. Upon enabling the method 400, the external programmer may display a message warning the physician that the presently programmed selection may result in a withholding of therapies and requesting confirmation of this selection.

When enabled, the method 400 begins at step 405 whenever microprocessor 224 detects a ventricular tachycardia based on VT detection criteria. VT detection criteria are typically defined by a programmed number of consecutively measured R-R intervals falling within a VT detection zone. At step 410, the tachycardia is classified as a slow VT or a fast VT based on the detected cycle length. Typically, a VT has a cycle length between 250 and 500 ms. A "slow" VT may generally be characterized by a cycle length between 450 to 500 ms and may be even longer, and a "fast" VT may generally be characterized by a cycle length of 250 to 300 ms. The tachycardia rate detection zones and detection criteria are preferably programmable parameters that allow selection of detection criteria to be tailored according to individual patient need.

If the initial VT detection is not a slow VT, as determined at decision step 410, anti-tachycardia therapies are delivered at step 430 according to programmed regimens, which can include anti-tachycardia pacing therapies and cardioversion shocks. If the initial VT detection is determined to be a slow VT at decision step 410, any anti-tachycardia pacing therapies programmed to be delivered in response to VT detection are delivered at step 420. At decision step 425, the microprocessor 224 determines if termination of the slow VT is detected. Termination is generally defined as a given number of consecutively sensed R-R intervals that are greater in length than the programmed VT detection interval. If anti-tachycardia pacing therapies have successfully terminated the slow VT, the method 400 is terminated at step 435.

If the microprocessor 224 does not detect termination at step 425 and continues to redetect slow VT at decision step 440 even after the programmed regimen of anti-tachycardia pacing therapies has been exhausted, the delivery of any programmed shock therapies is delayed at step 445. If, however, the slow VT has accelerated, as determined at decision step 440, then appropriate therapies are delivered at step 430 in response to the detected rhythm, either a fast VT or VF. An accelerated VT is generally detected when the sensed cycle length has shortened by a given interval, for example 60 ms, compared to the average cycle length before redetection.

If the slow VT did not accelerate, resulting in a delayed shock therapy at step 445, an optional patient notification signal may be generated by notification system 150 at step 447 to alert the patient that a therapy is being withheld. Such patient notification allows the patient to seek medical attention if desired. Notifying the patient that a shock therapy has been delayed also allows the patient to retire to a controlled setting for self-initiating a delayed shock therapy, such as at home resting rather than in a work place or driving a car.

After a shock therapy is delayed, the ICD 10 operates in a high alert mode as shown by step 500. The operations of the ICD 10 during the high alert mode 500 will be described later in greater detail with reference to the flow chart shown in FIG. 5.

Figure 4:
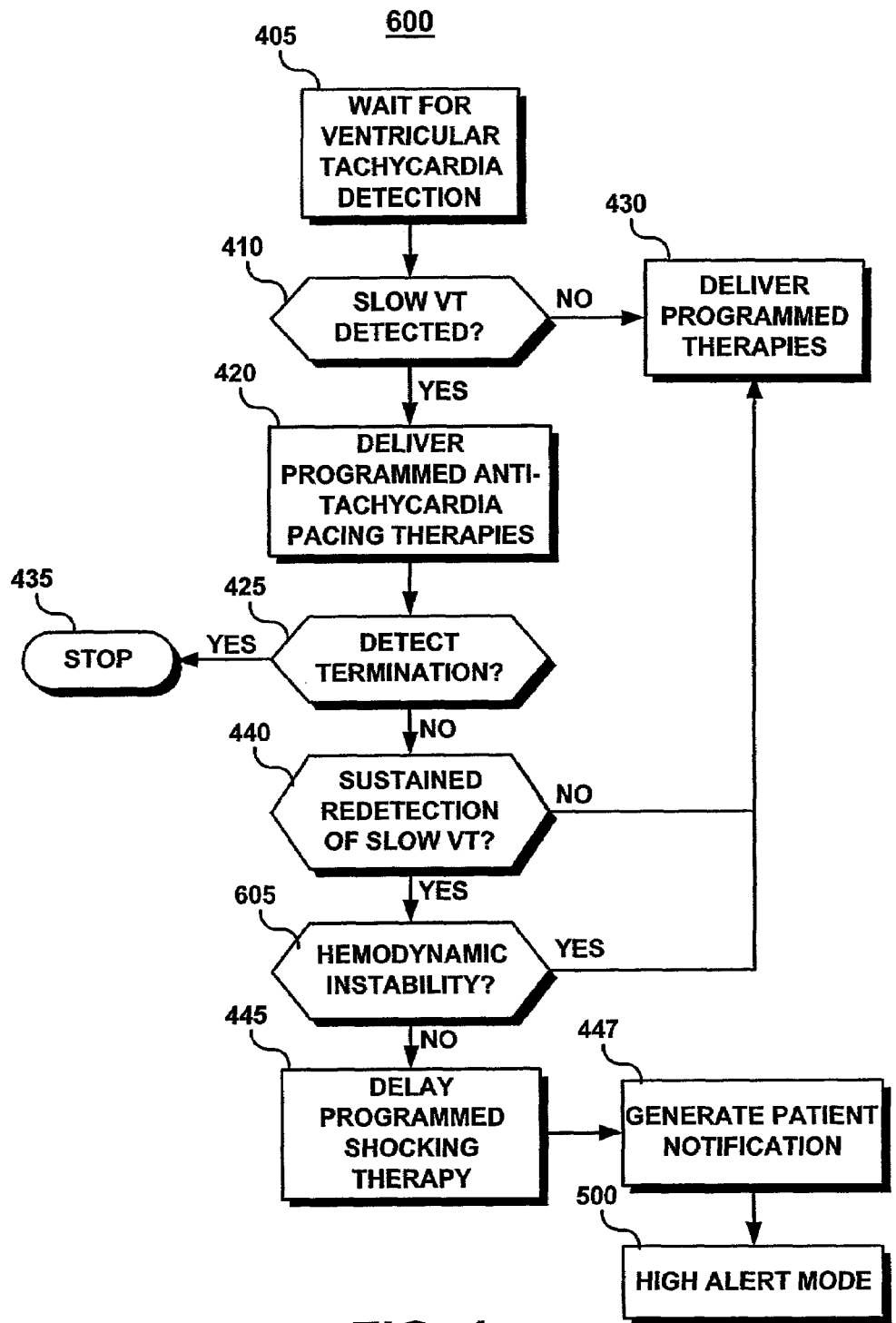
FIG. 4 is a flow chart illustrating a method for delaying a ventricular tachycardia therapy according to another embodiment of the present invention that includes hemodynamic monitoring.

FIG. 4 shows a flow chart summarizing a method 600 for delaying a shock therapy that includes monitoring a patient's hemodynamic status. In a preferred embodiment, the patient's hemodynamic status is a condition for delaying or delivering a shock therapy. In this embodiment, the sensor 344 provides a signal related to the hemodynamic status of the patient so that even during a slow VT a shock therapy is still delivered if the patient's hemodynamic status is compromised and pacing therapies were not successful in terminating the VT.

In one method of operation, a hemodynamic threshold level may be predetermined or programmable and stored in memory 226 for defining a compromised hemodynamic state. If the sensor processing circuit 342 determines that the hemodynamic status of the patient has deteriorated beyond the threshold level, a shock therapy is immediately initiated. In other methods of operation, a running average of a hemodynamic parameter may be determined and a change based on a percentage or the standard deviation of the average may be used to a detect a compromised hemodynamic state.

In FIG. 4, the steps 405 through 440 are performed exactly as described previously with reference to method 400 shown in FIG. 3. When a slow VT is detected (step 410), programmed anti-tachycardia pacing therapies are delivered (step 420). If termination is not detected (step 425) and the slow VT is sustained (step 440), the microprocessor 224 determines at step 605 if the patient is hemodynamically stable based on sensor processing 342 before delaying the shock therapy at step 445. At any time, if the detected rhythm is a fast VT or VF (steps 410 or 440), all programmed therapies, including shocks, are delivered (step 430). If a shock therapy is delayed (step 445) based on a slow VT detection and verification of stable hemodynamics at step 605, an optional patient notification may be delivered (step 447), and the ICD 10 begins operating in the high alert mode 500.

Figure 5:
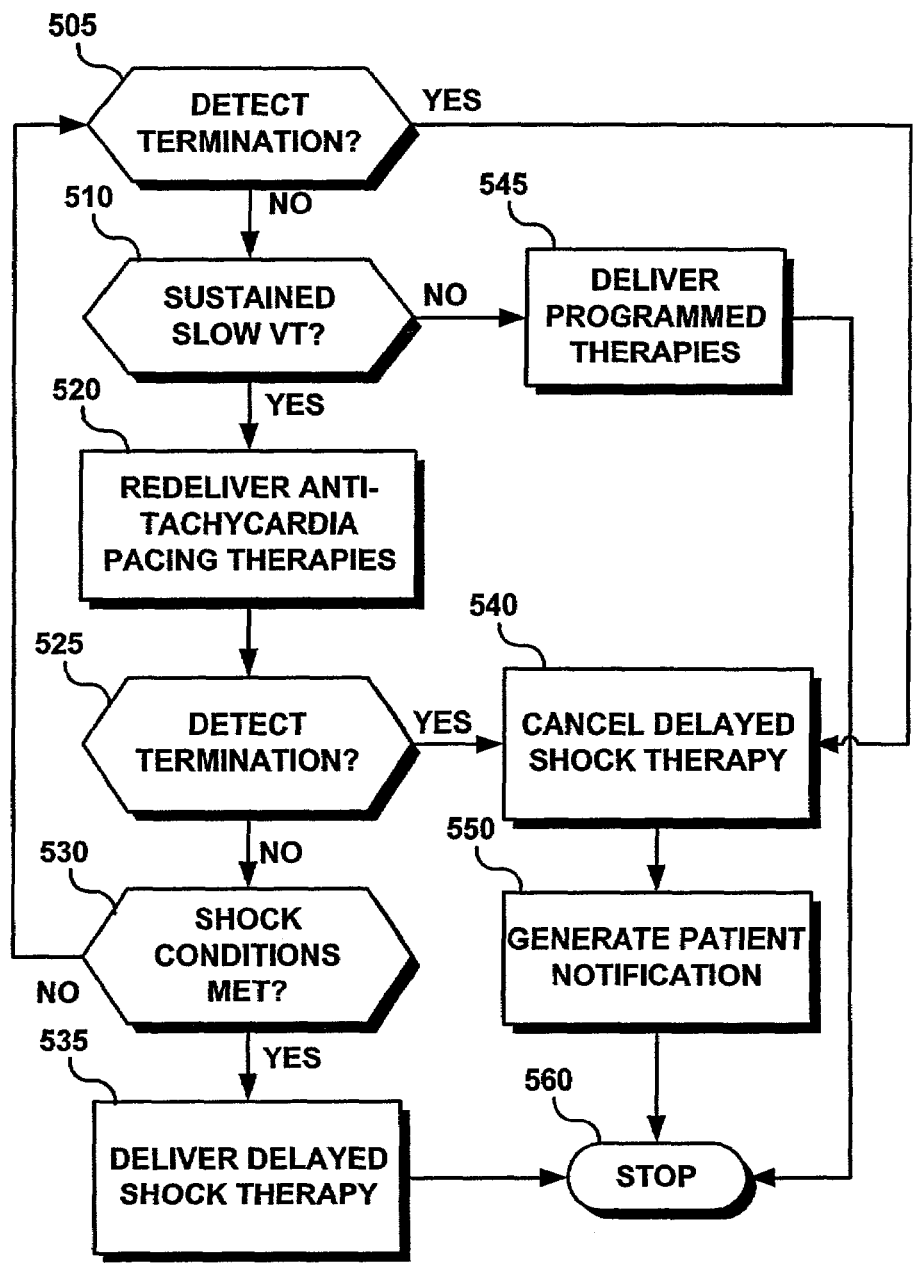
FIG. 5 is a flow chart illustrating the operations performed by the device shown in FIG. 2 during a period of delayed shock therapy.

Operations performed during the high alert mode are summarized by the flow chart shown in FIG. 5. The microprocessor 224 executes the method 500 to control when and if a delayed shock therapy will be delivered and to detect and respond quickly to any worsening of the heart rhythm. At decision step 505, microprocessor 224 continues to monitor for termination of the slow VT, which may still occur spontaneously during the shock delay period. If spontaneous termination is detected, the delayed shock therapy is canceled at step 540. In one embodiment, the optional patient notification system 150 may generate a second sound or voiced statement at step 550 to notify the patient that a withheld shock therapy is no longer needed and will not be delivered. The high alert mode 500 is then terminated at step 560.

If, however, termination is not detected, the ICD 10 continues to redetect the slow VT and remains on "high-alert" for detection of fast VT or VF at decision step 510. This high-alert mode allows the ICD 10 to detect a fast VT or VF more quickly than during the normal detection mode by using less stringent detection criteria. The detection criteria utilized during the high-alert mode may be similar to criteria used for redetection during a VT or VF episode. During a VT or VF episode, the number of intervals required for redetecting VT or VF after delivering a therapy is commonly programmed to be smaller than the number of intervals required for an initial VT detection. For example, twelve consecutive intervals shorter than the specified VT interval may be required to initially detect VT, whereas only eight intervals might be required to redetect VT after a therapy has been delivered. Similarly, fewer cardiac cycles may be required for redetecting VT or VF during the high-alert mode included in the present invention than for the initial VT/VF detection.

If the slow VT accelerates or becomes unstable, as determined at decision step 510 according to the less stringent high-alert detection criteria, programmed therapies, including cardioversion or defibrillation shocks, are immediately delivered at step 545 according to the detected rhythm. However, if the slow VT is sustained at decision step 510, the programmed anti-tachycardia pacing therapies that were delivered previously (at step 420, FIG. 4) are repeated at step 520, in a further attempt to terminate the slow VT without delivering a cardioversion shock. The pacing therapies may be repeated after a predetermined time interval, for example every five minutes or every hour. In one embodiment, pacing therapies may be re-delivered upon sensing a change in the heart rhythm that is thought to increase the likelihood of a successful termination. Reference is made to pending U.S. patent application Ser. No. 10/034,060 entitled "Automated Reapplication of Atrial Pacing Therapies", to Hess et al. filed on Dec. 20, 2001, incorporated herein by reference in its entirety. It is further recognized that a previously delivered regimen of pacing therapies may be repeated at step 520 or different regimens may be delivered in an alternating or cyclical fashion. Pacing therapies that are considered first tier therapies, in that they are not likely to induce VF, may be preferred over second tier pacing therapies that are known to be more likely to induce VF.

At decision step 525, the microprocessor 224 continues to monitor for termination of the slow VT, which may occur either spontaneously or in response to a successful anti-tachycardia pacing therapy. If termination is detected, the delayed shock therapy is cancelled at step 540, an optional patient notification is generated at step 550 and the method 500 is terminated at step 560.

If termination is not detected at decision step 525, the microprocessor 224 determines if a set of predefined conditions for delivering a delayed shock therapy are met at decision step 530. If these conditions are met, the delayed shock therapy is delivered at step 535. If these conditions are not met, the method 500 returns to step 505 and continues in the high alert mode, monitoring for termination or a worsening heart rhythm and repeating anti-tachycardia pacing therapies. This process, steps 505 through 530, continues until either termination is detected or the conditions required for delivering a delayed shock therapy are met.

One or more conditions, other than an accelerated heart rhythm, may be set as prerequisites for delivering a delayed shock therapy. In one embodiment, a required amount of time must elapse prior to delivering the delayed shock. Setting a predetermined amount of time until a delayed shock therapy is delivered and notifying the patient that a therapy is being withheld allows the patient to seek medical attention or become situated in a safe, resting position prior to shock delivery. By delaying the shock a given amount of time, the slow VT may spontaneously terminate during the delay period, or the repeated anti-tachycardia pacing therapies may be successful. In either case, the shock therapy is averted, and the patient is spared from receiving a painful shock. The predetermined amount of elapsed time may be on the order of hours but is preferably not longer than twenty-four hours. A sustained ventricular tachycardia, even if stable in the short term, can eventually lead to myocardial ischemia and symptoms of heart failure, making it undesirable to withhold VT therapy indefinitely.

In another embodiment, a required condition for delivery of a delayed shock therapy is detection of a prone position or a sudden change in position. Patients may experience dizziness and even fainting due to decreased cardiac output during ventricular tachycardia. A position sensor included in sensor 344 enables microprocessor 224 to detect a sudden change in position as evidence that the patient has fallen due to insufficient cardiac output. Detection of a sudden change in position by microprocessor 224 during a sustained slow VT, therefore, could trigger the delivery of a delayed shock therapy.

In another embodiment, a condition for delivering a delayed shock may be a determination that the patient is likely to be asleep. Any method for sleep detection known in the art may be used. For example, a combination of an activity sensor and a posture sensor may be used to detect a low level of activity and a prone position as evidence that the patient is likely to be asleep.

One risk of sustained ventricular tachycardia is the development of myocardial ischemia. Therefore, in one embodiment, an ischemia detection algorithm may be included in the ICD 10 for monitoring for myocardial ischemia during the high alert operating mode. Evidence of myocardial ischemia can be obtained from the sensed myocardial electrogram (EGM). In particular, ST-segment deviations detected in the sensed EGM signals can indicate myocardial ischemia. Any method for detecting myocardial ischemia known in the art may be used. One method for myocardial ischemia detection is described in U.S. Pat. No. 6,128,526 issued to Stadler et al., incorporated herein by reference in its entirety. If a condition of myocardial ischemia is detected during the high alert operation mode, the delayed shock therapy may immediately be delivered.

Figure 6:
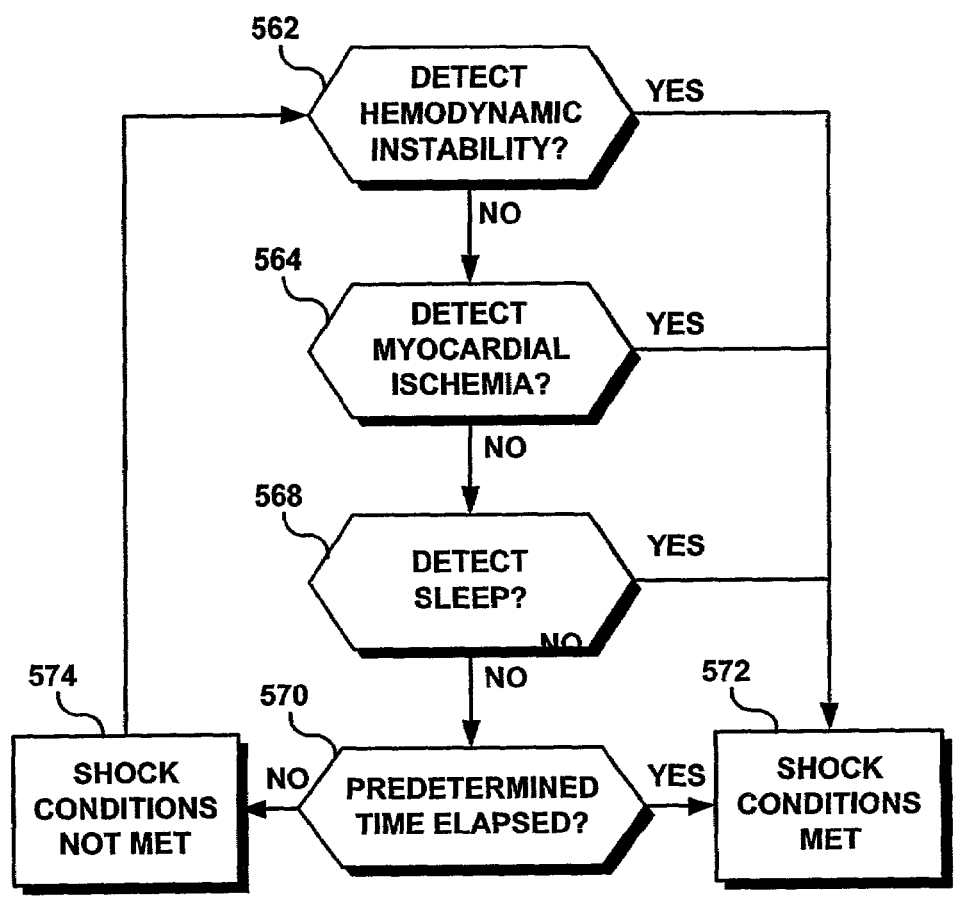
FIG. 6 is a flow chart illustrating the operations performed by the device shown in FIG. 2 for detecting conditions that will trigger the delivery of a delayed shock therapy.

It is recognized that any of a number of conditions or combination of conditions may be utilized for triggering a delayed shock therapy at step 530 during the high alert mode (FIG. 5). The flow chart shown in FIG. 6 summarizes one example of a number of conditions that may be tested for during step 530 of method 500 in order to determine if a delayed shock therapy needs to be delivered. At step 562, the microprocessor 224 determines if the patient is hemodynamically stable according to output from sensor processing 342 based one or more hemodynamic sensor signals obtained from sensor 344. If hemodynamic instability is detected, based on predetermined or programmable hemodynamic threshold settings, microprocessor 224 determines that the conditions for delivering a delayed shock therapy are met at step 572. The method 500 will then proceed to step 535 (FIG. 4) to deliver the delayed shock.

If hemodynamic instability is not detected at step 562, the microprocessor 224 screens for myocardial ischemia at step 564. If myocardial ischemia is detected, based on predetermined or programmable ischemia threshold settings, the conditions for delivering a delayed shock are met at step 572. If myocardial ischemia is not detected, the microprocessor 224 next determines if the patient is asleep at decision step 568. If sleep is detected, the shock conditions are met at step 572, and the delayed shock will be delivered. If none of the above conditions are met, the microprocessor 224 determines at step 570 if a predetermined delay time has elapsed in pacer timing and control 212. If the time has elapsed, the delayed shock will be delivered. If the delay time has not elapsed, the conditions for delivering a delayed shock are not met, as indicated at step 574, and steps 562 through 570 will be repeated. It is recognized that although the operations included in method 530 shown in FIG. 6 are illustrated as discreet steps, monitoring for the shock conditions may be performed continuously and simultaneously throughout the high-alert mode 500. In addition, any of these or other shock conditions may be programmed to be enabled or disabled by a clinician such that shock conditions can be tailored to individual patient need.

Figure 7:
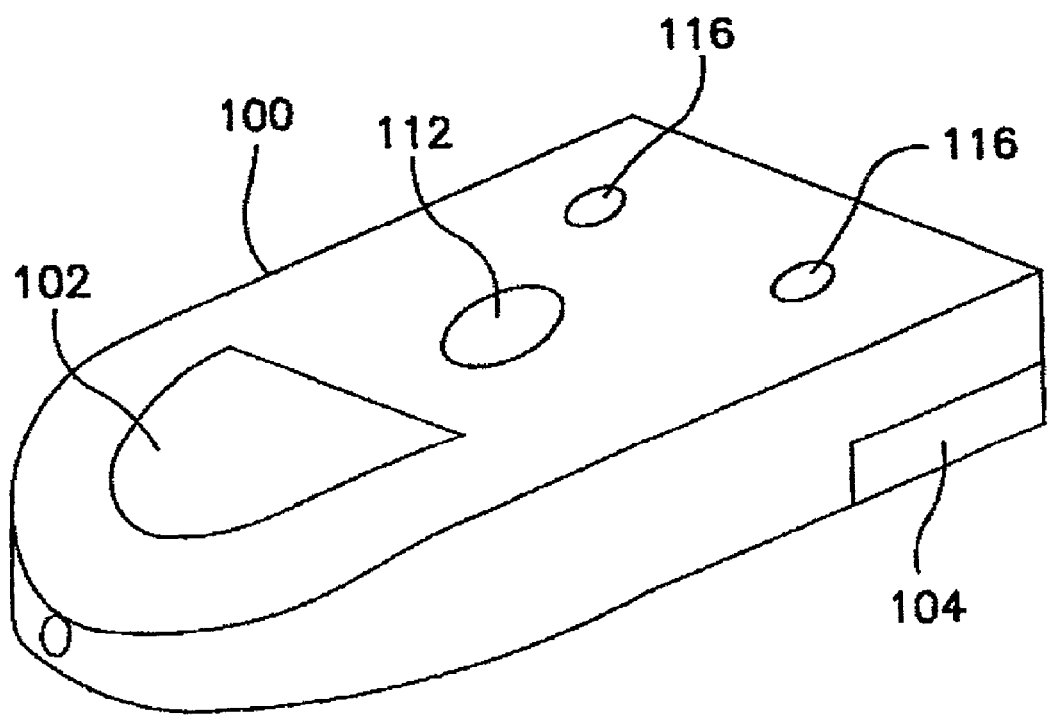
FIG. 7 is an illustration of a patient activator that may be used by a patient to trigger the delivery of a delayed therapy.

In yet another embodiment, the delayed shock therapy may be triggered by a patient or physician issued command anytime during the delay period. Such a command may be issued using an external programmer in communication with the ICD 10 via the telemetry circuitry 330. A command may also be given by a patient using a patient activator such as the type of activator shown in FIG. 7. A patient activator 100 is typically a hand-held device with a push button 102 that when depressed triggers the delivery of a therapy if the activator is positioned within telemetric communication distance from the implanted device. The activator 100 is generally battery-powered and provided with a battery compartment 104. A speaker 112 is provided for broadcasting patient alert signals during telemetric communication with the ICD 10. Two, differently colored LEDs 116 are provided for signaling information regarding the status of a patient-triggered therapy.

Alternative patient-initiated triggers for delivering a delayed shock therapy may include a specific action by the patient. For example, breath-holding by the patient in an effort to brace himself for a pending shock may be sensed by an impedance sensor included in ICD 10. In another example, tapping on the implanted ICD 10 by the patient may be sensed by a piezoelectric crystal located within the ICD 10 housing. When a shock therapy is delayed, the patient may be alerted to the need for a shock therapy by the patient notification system 150 within ICD 10. The patient may then initiate the shock therapy at a time when the patient is ready to receive it using the patient activator 100 or an alternative patient-initiated trigger. For details regarding a general patient activator and other exemplary forms of patient initiated triggers, reference is made to the previously incorporated U.S. Pat. No. 5,987,356 issued to DeGroot.

Thus, a method and apparatus have been described for delaying the delivery of a shock therapy in a patient having hemodynamically stable, low rate ventricular tachycardia. Using the methods included in the present invention, the incidence of painful shock therapies can be minimized or all together avoided in patients diagnosed with recurring, non-life threatening ventricular tachycardia. By reducing the number of delivered shock therapies, the battery longevity of an implantable pacemaker cardioverter defibrillator device is extended. Delaying a scheduled shock therapy can avoid further risk to the patient by allowing the delivered therapy to occur at a time when the patient is in a controlled situation. These benefits may be realized by implementing the present invention according to the exemplary embodiments disclosed herein. However, it will be understood by one skilled in the art that variations or modifications to the described embodiments may be made without departing from the scope of the present invention. As such, the exemplary embodiments disclosed herein should not be considered limiting with regard to the following claims.

What is claimed is:

1. A method for controlling the delivery of a shock therapy in a cardiac patient experiencing ventricular tachycardia, comprising:

detecting a ventricular tachycardia;

delivering an anti-tachycardia pacing therapy when said ventricular tachycardia is detected;

determining if the ventricular tachycardia is terminated after said anti-tachycardia pacing therapy is delivered; and delaying a programmed shock therapy based on measures of patient hemodynamic state, wherein said measures of hemodynamic state are made with respect to hemodynamic threshold criteria that establish a cardiac patient hemodynamic stable state.

2. The method of claim 1, further comprising:

setting a hemodynamic threshold criteria;

detecting a hemodynamic state of the patient; and delaying said programmed therapy based on comparing said hemodynamic state of the patient against said hemodynamic threshold criteria.

3. The method of claim 2 wherein said method further comprising:

defining a condition for delivering a delayed shock therapy; and delivering said delayed shock therapy when the condition for shock delivery is satisfied.

4. The method of claim 3 wherein said condition for delivering a delayed shock therapy includes detecting a hemodynamic state that does not meet said hemodynamic threshold criteria.

5. The method according to claim 3 wherein said condition for delivering a delayed shock therapy includes monitoring a specified amount of elapsed time.

6. The method according to claim 1 further comprising:

defining a condition for delivering a delayed shock therapy; and delivery said delayed shock therapy when said condition for delivering is satisfied.

7. The method according to claim 6, further including detecting a posture of the patient.

8. The method according to claim 11 wherein said condition for delivering a shock therapy includes detection of a sudden change in the patient's position.

9. The method of claim 6 further including detecting a sleeping state of the patient.

10. The method of claim 9 wherein a condition for delivering said delayed shock therapy includes detection of a sleeping state.

11. The method of claim 6 further including detecting myocardial ischemia.

12. The method of claim 6 wherein shock therapy is delivered by the patient or physician.

13. A device-implemented software system for controlling the delivery of a shock therapy in a cardiac patient experiencing ventricular tachycardia, the system comprising:

means for detecting a ventricular tachycardia;

means for identifying if slow ventricular tachycardia is detected;

means for delivering programmed anti-tachycardia pacing therapies;

means for detecting termination of the ventricular tachycardia;

means for detecting sustained slow ventricular tachycardia;

means for checking hemodynamic instability;

means for delaying programmed shock therapy; and means for generating patient notification, wherein said means for detecting termination cooperates with said means for detecting sustained slow ventricular tachycardia.

14. The system of claim 13 wherein said means for checking hemodynamic instability cooperates with means for detecting myocardial ischemia, means for detecting sleep, means for marking predetermined time elapsed and means for confirming if one of shock conditions met and shock conditions not met.

15. The system of claim 13 wherein said means for generating patient notification further includes means for signaling a high alert mode.

* * * * *

UNITED STATES PATENT AND TRADEMARK OFFICE
CERTIFICATE OF CORRECTION

| | | |
|---|---|---|
| PATENT NO. | : 7,010,344 B2 | Page 1 of 1 |
| APPLICATION NO. | : 10/134352 | |
| DATED | : March 7, 2006 | |
| INVENTOR(S) | : John E. Burnes et al. | |

It is certified that error appears in the above-identified patent and that said Letters Patent is hereby corrected as shown below:

Claim 8, Col. 13, line 19, delete "The method according to claim 11..."

and insert in place there of -- The method according to claim 7... --.

Signed and Sealed this

Seventeenth Day of March, 2009

JOHN DOLL
*Acting Director of the United States Patent and Trademark Office*